United States Patent
Meinecke et al.

(10) Patent No.: US 6,526,369 B1
(45) Date of Patent: Feb. 25, 2003

(54) APPARATUS AND PROCESS FOR A CROSS-DIRECTION PROFILE OF A MATERIAL WEB

(75) Inventors: Albrecht Meinecke, Heidenheim (DE); Rudolf Münch, Königsbronn (DE)

(73) Assignee: Voith Sulzer Papiertechnik Patent GmbH, Heidenheim (DE)

( * ) Notice: Subject to any disclaimer, the term of this patent is extended or adjusted under 35 U.S.C. 154(b) by 0 days.

(21) Appl. No.: 09/353,021

(22) Filed: Jul. 13, 1999

(30) Foreign Application Priority Data

Jul. 14, 1998 (DE) .......................... 198 31 612

(51) Int. Cl.⁷ .......................... G01B 5/02; G01B 11/02; G01B 13/02
(52) U.S. Cl. .......................... 702/170; 702/40; 702/172
(58) Field of Search .......................... 702/33, 34, 36, 702/40, 81–84, 97, 155–159, 170, 172, 183, 189; 250/359.1, 341.8, 339.11, 341.1, 339.06, 559.01, 559.04; 162/198, 50

(56) References Cited

U.S. PATENT DOCUMENTS

| | | | | |
|---|---|---|---|---|
| 2,909,660 A | * | 10/1959 | Alexander | 118/672 |
| 3,531,827 A | * | 10/1970 | Dragonette | 250/359.1 |
| 3,614,450 A | * | 10/1971 | Hill et al. | 162/263 |
| 4,767,935 A | | 8/1988 | Anderson | 250/559.04 |

(List continued on next page.)

FOREIGN PATENT DOCUMENTS

| | | | | |
|---|---|---|---|---|
| DE | 4001650 | 8/1990 | | |
| DE | 4232529 | 3/1994 | | |
| DE | 4422400 | 1/1996 | | |
| DE | 4422861 | 1/1996 | | |
| DE | 19627456 | 1/1998 | | |
| DE | 29804040 | 6/1998 | | |
| DE | 19732831 | 2/1999 | | |
| EP | 0390623 | 10/1990 | | |
| EP | 0458168 | 11/1991 | | |
| EP | 0731350 | 9/1996 | | |
| EP | 0731913 | 9/1996 | | |
| EP | 0735501 | 10/1996 | | |
| GB | 1378303 | * | 12/1974 | G01N/21/30 |
| WO | 93/08925 | 5/1993 | | |
| WO | 95/15492 | 6/1995 | | |
| WO | 97/33139 | 9/1997 | | |

OTHER PUBLICATIONS

*Wochenblatt für Papierfabrikation*, No. 11/12, p. 609 and 611 (1998).

Primary Examiner—Marc S. Hoff
Assistant Examiner—Manuel L. Barbee
(74) Attorney, Agent, or Firm—Greenblum & Bernstein, P.L.C.

(57) ABSTRACT

Measurement system and process for measuring a cross-direction profile of specific properties of at least one of a material web and a coating on the material web. The system includes at least one stationary cross-direction profile measurement device having at least one radiation source adapted to irradiate the at least one of the material web and the coating on the material web in a plurality of defined and different wavelength ranges, and at least one sensor adapted to measure the intensity of radiation affected by the at least one of the material web and the coating on the material web. The system also includes at least one measurement and/or evaluation electronics system. Each sensor detects only one of the defined different wavelength ranges of the radiation at a specific point in time. The process includes irradiating the at least one of the material web and the coating on the material web with a plurality of defined and different wavelength ranges via at least one radiation source, and measuring an intensity of radiation affected by the at least one of the material web and the coating on the material web with at least one sensor. Only one of the defined different wavelength ranges of the radiation is measured by each sensor at a specific point in time.

38 Claims, 1 Drawing Sheet

U.S. PATENT DOCUMENTS

| | | | | |
|---|---|---|---|---|
| 4,786,817 A | * | 11/1988 | Boissevain et al. | 250/339.1 |
| 5,019,710 A | | 5/1991 | Wennerberg et al. | 280/341.7 |
| 5,071,514 A | | 12/1991 | Francis | 162/259 |
| 5,073,712 A | | 12/1991 | Hellstrom | 250/252.1 |
| 5,172,005 A | | 12/1992 | Cochran et al. | 250/559.08 |
| 5,277,928 A | * | 1/1994 | Strandberg | 118/420 |
| 5,357,335 A | | 10/1994 | Sparks et al. | 356/237.2 |
| 5,365,084 A | * | 11/1994 | Cochran et al. | 250/226 |
| 5,563,809 A | * | 10/1996 | Williams et al. | 700/122 |
| 5,715,158 A | | 2/1998 | Chen | 700/300 |
| 5,724,093 A | | 3/1998 | Parenti | 348/131 |
| 5,745,365 A | | 4/1998 | Parker | 700/122 |
| 5,822,070 A | * | 10/1998 | Syre | 250/339.02 |

* cited by examiner

APPARATUS AND PROCESS FOR A CROSS-DIRECTION PROFILE OF A MATERIAL WEB

CROSS-REFERENCE TO RELATED APPLICATIONS

The present application claims priority under 35 U.S.C. §119 of German Patent Application No. 198 31 612.7 filed on Jul. 14, 1998, the disclosure of which is expressly incorporated by reference herein in its entirety.

BACKGROUND OF THE INVENTION

1. Field of the Invention

The present invention concerns a measurement system and process for measuring the cross-direction profile of specific properties of a material web, e.g., a paper or cardboard web, in a paper and/or cardboard machine or in a coating machine.

2. Discussion of Background Information

Measurement systems which are similar in general to above-described measurement systems and commonly known operate on the basis of IR-, $\alpha$-, $\beta$-, and $\gamma$-rays with traversing measurement arrangements. Further, as disclosed in "Wochenblatt für Papierfabrikation [Paper Fabrication Weekly]", Vol. 11/12, p. 609 and 611 (1998), non-traversing measurement devices which are designed for spectroscopic measurement immediately downstream from the headbox of a paper machine are also known.

Among other disadvantages, the known measurement systems require measurements to be taken mainly in long, free stretches of the material web. In conventional traversing measurement systems, a pure cross-directional profile measurement is virtually excluded since the traversing movement entails a sort of zigzag scanning. Measurement is normally possible only in the wire section and at the end of a respective paper machine, however, excessively long operating cycles tend to result due to the large number of final control elements lying between, which causes relatively imprecise control.

The use of CCD cameras for measuring surface weight is already known. It is true that these devices can detect the entire paper surface produced. However, the expensive image processing is particularly disadvantageous.

Measurement devices for measuring conductivity of the material on the wire in the wet section are also known. While these measurement devices can be arranged relatively near the headbox control elements in question, a disadvantage is that conductivity is a measure of moisture and not of surface weight. Thus, for example, an application for coaters is excluded.

SUMMARY OF THE INVENTION

The present invention creates an improved measurement system of the type generally discussed above which eliminates the above-noted disadvantages, and which ensures shorter control times and more accurate control.

Thus, the apparatus of the present invention includes at least one stationary cross-direction profile measurement device that includes at least one radiation (illumination) source positioned to irradiate (illuminate) the material web in a plurality of defined different wavelength ranges and at least one sensor positioned to measure the intensity of radiation which has been affected by the material web. The apparatus also includes at least one measurement and/or evaluation electronic system. The at least one sensor is adapted to measure only one of the plurality of defined different wavelength ranges of the radiation at a time.

Based on the design according to the present invention, a more accurate measurement of the cross-direction profile of specific properties is possible while reducing space requirements and increasing economy. Moreover, it is possible to take measurements at relatively inaccessible points, e.g., areas of closed travel, in which the material web is supported, e.g., by a roll, a belt, a sieve, and/or a felt. In this regard, radiation reflected by the material web or a coating on the material web can be detected by at least one sensor. Additionally or alternatively, radiation which has passed through the material web or a coating on the material web can be detected by at least one sensor. The detection of reflected radiation from the material web or a coating on the material web advantageously requires less space.

According to an exemplary embodiment of the present invention, at least two stationary cross-direction profile measurement devices can be spaced in a web travel direction of travel. Advantageously, these spaced apart at least two stationary cross-direction profile measurement devices can be associated with at least one unit of a web production machine, e.g., a press section, a dryer section, and/or of a coating machine. The web production machine may produce, e.g., paper webs and/or cardboard webs.

In particular, the present invention can be utilized to reduce control times. For example, it can be advantageous to position at least one stationary cross-direction profile measurement device immediately before and/or immediately after at least one actuator or control element, which is provided to control the respective cross-direction profile.

Based upon the design according to the present invention, it may be possible to provide at least one stationary cross-direction profile measurement device in at least the press section and/or dry section of a paper and/or cardboard machine.

Alternatively or additionally, at least one stationary cross-direction profile measurement device may be provided in at least the wire section and/or at the end of a paper and/or cardboard machine.

A filter device or element may be provided to filter out specific disturbance variables and/or the influence of at least one actuator or control element on the respective cross-direction profile. For example, exponential filters or moving average filters can be utilized. Moreover, more sophisticated filters, such as Kalman filters, may also be utilized.

In order to reduce the space requirement and increase the economy of operation, it may be expedient to connect the radiation source and/or the sensor to at least one light guide.

Moreover, the at least one stationary cross-direction profile measurement device can be designed for operation in the near infrared range (NIR).

At least one stationary cross-direction profile measurement can be designed, e.g., for quantitative detection of surface weight, moisture, thickness, specific ingredients, and/or other properties of the material web.

In particular, for measuring in regions of a free web stretch, a respective stationary cross-direction profile measurement can be provided with at least one optical radiation source to irradiate the material web and can include at least one photodetector to measure the intensity of the optical radiation affected by the material web.

If the material web is irradiated via a plurality of radiation sources of different wavelength ranges, the material web can be irradiated, e.g., by the individual different radiation sources and/or by different chronologically consecutive combinations of radiation sources.

In another advantageous embodiment of the measurement system according to the present invention, at least one stationary cross-direction profile measurement device may be provided with a plurality of sensors of different spectral sensitivity. In this manner, the respective stationary cross-direction profile measurement device preferably includes only one radiation source to irradiate the material web.

In principle, it is possible to provide at least one sensor/filter unit having a spectral sensitivity and/or permeability that is adjustable.

In an exemplary embodiment, at least one light-emitting diode may be provided as a radiation source, which can be particularly advantageous in view of the longevity of service as well as the low cost of such components. Thus, a long-standing prejudice, i.e., that such light-emitting diodes are allegedly not suitable for this purpose, is also overcome by the present invention.

In a wavelength range from 1300 to 2400 nm, there can be relatively strong peaks in the absorption spectrum, e.g., approximately 1450 nm water-overtone, approximately 1930 nm water, approximately 2100 nm cellulose fiber, approximately 2010 nm clay, approximately 2300 nm latex and lignin, approximately 2300–2400 nm polyethylene and other plastics, for which light-emitting diodes are not currently available or are too expensive. Accordingly, up to now, lamps with incandescent filaments have been utilized. However, investigations have demonstrated that conclusions can absolutely be drawn with multiple LEDs of different wavelengths, e.g., surface weight and, if necessary, other web properties. Thus, the relative measurement accuracy, i.e., the responsiveness of a respective sensor to very small fluctuations of properties, can be very high. The longer service life of LEDs compared to lamps with filaments is critical because, for the application of the cross-direction profile measurement, between 50 and 500 sensors may be customarily used simultaneously, and it unreasonable for the operator be continually dealing with lamp failures. This list of wavelengths is not exhaustive, i.e., if more or other wavelengths are believed interesting to the user, it becomes simply a matter of trying it in a special application and collecting empirical data. If a wavelength proves interesting, it is noted that an illumination source and the sensors should be selected appropriately.

Moreover, the present invention has an extremely small space requirement which reduces back scattering. Ideal applications in this case are, for example:

fiber deposit on the sieve (screen) in the wet section;

paper on a felt in the press, on a drying felt, or on a drying wire;

paper on a metal surface (e.g., roller);

coating deposit on a color application roll (e.g., speed coater);

coating on a paper web;

Alternatively, or additionally,, a measurement in the transmitted light method is also possible, however, this may be associated with a higher cost of operation.

In an exemplary embodiment, at least one stationary cross-direction profile measurement device may be provided with a device to spectrally divide an optical beam affected by the material web on the sensor side. The stationary cross-direction profile measurement device can include a photodiode array which can be exposed to the divided beam with, for example, at least 16 sensors, and preferably 256. Alternatively, a digital cameral can be considered as a special photodiode array which can be utilized with the stationary cross-direction profile measurement device. Further, the digital camera can also be utilized in place of a plurality of single sensors so as to derive the cross-direction profile by imaging operations.

Expediently, at least one stationary cross-direction profile measurement device can be provided with multiple radiation sources of different wavelength ranges to irradiate the material web.

The radiation sources can be provided in a common enclosure and, consequently, appear from the outside as a single radiation source in which the type of radiation emitted can be altered depending on electrical inputs. Thus, a lamp with multiple different filaments is conceivable.

The measurement and/or evaluation electronics can advantageously include a unit to irradiate the material web with at least one stationary cross-direction profile measurement device via individual radiation sources of different wavelength ranges and/or via different combinations of radiation sources one after another in time.

An additional conclusion about the absorption at different wavelengths may be possible, e.g., when at least two sensors disposed at different distances relative to the radiation sources are used.

In principle, it is also possible that at least one separate sensor or a separate sensor pair can be associated with the radiation sources of at least one stationary cross-direction profile measurement device. In this case, the space used is, consequently, somewhat greater. However, it is advantageous that the measurement results obtained by the sensors can be queried simultaneously.

In an another embodiment of the measurement system according to the present invention, at least one stationary cross-direction profile measurement device may preferably include three optical radiation sources and at least one sensor for each measurement point. Thus, at least three signals are available in each case. The necessary hardware can be integrated simply, requires little space on the machine, and can be produced very inexpensively.

According to an advantageous practical embodiment, at least one stationary cross-direction profile measurement device may preferably include at least one infrared light-emitting diode for each measurement point (e.g., 880 nm or 950 nm), a red light-emitting diode (e.g., 635 nm), and a blue light-emitting diode (e.g., 480 nm or a gallium nitrite LED with 430 nm).

The radiation angle of the light-emitting diodes has a significant influence on the measurement process. Preferably, at least one stationary cross-direction profile measurement device can be provided with at least one light-emitting diode whose radiation angle lies in a range, e.g., between approximately 12° and approximately 30°. The distance to the surface or the coating of the material web lies expediently in a range, e.g., between approximately 5 and approximately 20 mm.

The switching frequency of the light-emitting diodes should be high compared with the time-slot pattern in which the property measurement data are acknowledged, and is limited by the cutoff frequency of the sensors and the light-emitting diodes as well as the speed of the evaluation electronics. For example, approximately 1000 switching operations per second or more are conceivable in practice. Thus, it is possible to obtain, e.g., a property measurement value approximately every 0.5 seconds, which itself is in turn generated by the evaluation of more than 500 individual measurements. The same result can also be obtained, e.g., in that a switching frequency of approximately 50 Hz can be selected and 10 individual measurement values are taken after a switchover operation.

From the measurement data obtained, it can be possible to draw conclusions concerning, e.g., the most important characteristics of the material web by comparison with empirical data. For example, it has been demonstrated that a general surface weight change has roughly the same effect in all measurement signals, whereas a change in other properties has very different effects on these signals. Thus, it is possible to verify through experimentation, how a change in moisture affects the measurement signals. Moreover, these findings can be incorporated into an evaluation algorithm. In the measurement and/or evaluation electronics, this algorithm can then used to quantitatively determine, e.g., the different properties from the measurement signals. For example, empirically determined relationships between wavelengths and material properties, as discussed above, can be experimentally determined. Further, relationships related to the amplitudes of the signals, e.g., absolute sensor readings at given wavelengths related to the material properties, can be useful. Because the absolute values depend, e.g., on the color or other ingredients, whether known or unknown, of the paper, the sensors should be calibrated by performing test measurements that can be compared to lab measurements or otherwise known material properties. In this manner, the empirical data can be collected. In an example in which three LEDs are utilized, e.g., an infrared, a red, and a blue LED, the infrared LED generally provides the strongest response with respect to fiber constant changes, whereas the blue LED gives a strongest response with respect to ash content changes. The amplitudes depend on, e.g., paper grade, etc. Thus, calibration is based upon the empirical data, and the mathematics behind calibration is generally known. For example, the least partial squares method can be used, as well as any other known methods.

In the embodiment of the measurement system according to the present invention, the measurement and/or evaluation electronics can be simultaneously associated with multiple cross-direction profile measurement devices. Moreover, it may be preferable that each of the multiple cross-direction profile measurement devices are stationary.

By selecting a respective measurement location as near as possible to the adjustment point affected, a substantially responsive control element can be associated unequivocally and immediately with a relevant measurement position on the material web or its coating. In this way, the measurement point and the actuator or control permit rapid control through the shared electronics. If the actuators act to a considerable extent in the width, the actuator electronics can mutually obtain information relative to their adjustments so that, at the time of an adjustment, each actuator can take into consideration how the others are already adjusted.

Thus, a loss of time, would otherwise occur for the transmission of data to, e.g., a measurement logging computer, to, e.g., a cross-direction profile computer, to, e.g., the relevant control element or actuator, may be avoided.

For example, in connection with a "speed coater," an underlying control circuit can keep the layer thickness constant on the application roll. A superimposed control circuit can take care of proper maintenance of, e.g., absolute values of the coating application.

The present invention is directed to a measurement system for measuring a cross-direction profile of specific properties of at least one of a material web and a coating on the material web. The system includes at least one stationary cross-direction profile measurement device having at least one radiation source adapted to irradiate the at least one of the material web and the coating on the material web in a plurality of defined and different wavelength ranges, and at least one sensor adapted to measure the intensity of radiation affected by the at least one of the material web and the coating on the material web. The system also includes at least one measurement and/or evaluation electronics system. Each sensor detects only one of the defined different wavelength ranges of the radiation at a specific point in time.

According to a feature of the instant invention, the at least one stationary cross-direction profile measuring device can include at least two stationary cross-direction profile measurement devices spaced in the direction of travel of the web. The at least one of the material web and the coating on the material web is located within at least one of a paper, a cardboard, and a coating machine. The at least two stationary cross-direction profile measurement devices are positioned such that one of the at least two stationary cross-directional profile measurement devices is positioned near an end of the at least one paper, cardboard, and coating machine, and another of the at least two stationary cross-directional profile measurement devices is positioned one of in and before a headbox of the at least one paper, cardboard, and coating machine.

In accordance with another feature of the present invention, at least one actuator and control element can be provided to adjust the cross-direction profile, and the at least one stationary cross-direction profile measurement device may be arranged at least one of immediately before and immediately after at least one actuator and control element.

In accordance with still another feature of the instant invention, the at least one stationary cross-direction profile measurement device may be located in at least one of a press section and a dry section of one of a paper and cardboard machine.

According to a further feature of the present invention, the at least one stationary cross-direction profile measurement device can be located in a region of closed web travel.

According to another feature of the instant invention, the at least one stationary cross-direction profile measurement device may be located in at least one of a wire section and at an end of one of a paper and cardboard machine.

In accordance with a still further feature of the present invention, a filter device may be provided to filter out at least one of specific disturbance variables and the influence of at least one of an actuator and control element on a respective cross-direction profile.

In accordance with still another feature of the present invention, at least one of the at least one radiation source and the at least one sensor can be connected to at least one light guide.

According to another feature of the instant invention, the at least one stationary cross-direction profile measurement device can be adapted to operate in the near infrared range (NIR).

According to still another feature of the present invention, the at least one stationary cross-direction profile measurement device can be adapted to quantitatively detect at least one of surface weight, moisture, thickness, and specific ingredients of the at least one of the material web and the coating on the material web.

In accordance with a further feature of the present invention, the at least one sensor can be adapted to detect radiation passing through at least one of the at least one of the material web and the coating on the material web and a coating of the at least one of the material web and the coating on the material web.

In accordance with a still further feature of the present invention, the at least one sensor can be adapted to detect radiation reflected by at least one of the at least one of the material web and the coating on the material web and a coating on the at least one of the material web and the coating on the material web.

According to still another feature of the instant invention, the at least one stationary cross-direction profile measurement device can include at least one optical radiation source adapted to irradiate th e at least one of the material web and the coating on the material web, the at least one optical radiation source may include at least one photodetector adapted to measure the intensity of the optical radiation affected by the at least one of the material web and the coating on the material web.

According to another feature of the present invention, the at least one sensor can include a plurality of sensors having different spectral sensitivities, and the at least one radiation source can include only one radiation source.

In accordance with still another feature of the instant invention, at least one of the at least one sensor and a filter unit has one of an adjustable spectral sensitivity and adjustable permeability.

In accordance with a further feature of the instant invention, the at least one radiation source may include at least one light-emitting diode.

In accordance with a still further feature of the present invention, the at least one stationary cross-direction profile measurement device can include a device to spectrally divide optical radiation affected by the at least one of the material web and the coating on the material web on a sensor side, and the device to spectrally divide optical radiation includes a photodiode array with at least 16 sensors adapted to be acted upon by the divided radiation.

In accordance with still another feature of the present invention, the at least one stationary cross-direction profile measurement device can include a device to spectrally divide optical radiation affected by the at least one of the material web and the coating on the material web on a sensor side. The device to spectrally divide optical radiation includes a photodiode array with at least 256 sensors adapted to be acted upon by the divided radiation.

According to another feature of the instant invention, the at least one radiation source may include a plurality of radiation sources having different wavelength ranges, and the plurality of radiation sources may be adapted to irradiate the at least one of the material web and the coating on the material web. Further, the at least one radiation source can include a plurality of radiation sources. The at least one measurement and/or evaluation electronics can be adapted to irradiate the at least one of the material web and the coating on the material web with at least one of a plurality of different wavelength ranges and chronologically consecutive combinations of the plurality of radiation sources.

In accordance with still another feature of the instant invention, the at least one stationary cross-direction profile measurement device can include at least two sensors arranged at different distances relative to the at least one radiation source.

According to another feature of the present invention, one of an additional sensor and an additional sensor pair can be adapted to be used with the at least one radiation source.

According to a further feature of the instant invention, the at least one radiation source may include three optical radiation sources and the least one sensor may include at least one sensor adapted for use at each measurement point.

According to a still further feature of the invention, the at least one radiation source may include at least one infrared, at least one red, and at least one blue light-emitting diode.

In accordance with still another feature of the invention, the at least one radiation source may include at least one of an infrared, a red, and a blue light-emitting diode.

According to a further feature of the instant invention, the at least one radiation source may include at least one light-emitting diode having a radiation angle within a range between approximately 12° and approximately 30°.

In accordance with yet another feature of the present invention, the at least one stationary cross-direction profile measurement device may include a plurality of stationary cross-direction profile measurement devices. The at least one measurement and/or evaluation electronics system may be simultaneously associated with more than one stationary cross-direction profile measurement device of the plurality of stationary cross-direction profile measurement devices.

According to yet another feature of the instant invention, the at least one sensor may include a digital camera.

The present invention is also directed to a process for measuring a cross-direction profile of specific properties of at least one of a material web and a coating on the material web. The process includes irradiating the at least one of the material web and the coating on the material web with a plurality of defined and different wavelength ranges via at least one radiation source, and measuring an intensity of radiation affected by the at least one of the material web and the coating on the material web with at least one sensor. Only one of the defined different wavelength ranges of the radiation is measured by each sensor at a specific point in time.

According to a feature of the invention, the process may further include adjusting the cross-direction profile with at least one of an actuator and a control element.

In accordance with another feature of the instant invention, the irradiating and measuring can be performed in a region of closed web travel.

In accordance with a further feature of the present invention, the process may further include filtering out at least one of specific disturbance variables and the influence of at least one of an actuator and a control element on a respective cross-direction profile.

In accordance with still another feature of the invention, the process may further include operating the at least one radiation source in the near infrared range (NIR).

According to a still further feature of the present invention, the process may further include quantitatively detecting at least one of surface weight, moisture, thickness, and specific ingredients of the at least one of the material web and the coating on the material web.

According to still another feature of the present invention, the process can further include detecting radiation passing through at least one of the at least one of the material web and the coating on the material web and a coating of the material web.

In accordance with yet another feature of the present invention, the process can further include detecting radiation reflected by at least one of the material web and a coating on the material web.

The present invention is also directed to a process for determining a cross-direction profile of specific properties of at least one of a material web and a coating on the material web with an apparatus that includes at least one radiation source, at least one sensor, and at least one set of measurement electronics. The process includes positioning the apparatus in a press section of at least one of a paper, a cardboard, and a coater machine, irradiating at least one of the material web and the coating on the material web in the press section with the at least one radiation source in the plurality of defined and different wavelength ranges, and measuring the intensity of the radiation that has been affected by the at least one of the material web and the coating on the material web with the at least one sensor. The at least one sensor detects only one of the defined and different wavelength ranges of the radiation at a time.

The present invention is also directed to a process for determining a cross-direction profile of specific properties of at least one of a material web and a coating on the material web with an apparatus that includes at least one radiation source, at least one sensor, and at least one set of measurement electronics. The process includes positioning the apparatus in a dryer section of at least one of a paper, a cardboard, and a coater machine, irradiating at least one of the material web and the coating on the material web in the dryer section with the at least one radiation source in the plurality of defined and different wavelength ranges, and measuring the intensity of the radiation that has been affected by the at least one of the material web and the coating on the material web with the at least one sensor. The at least one sensor detects only one of the defined and different wavelength ranges of the radiation at a time.

The instant invention is also directed to a process for determining a cross-direction profile of specific properties of at least one of a material web and a coating on the material web with an apparatus that includes at least one radiation source, at least one sensor, and at least one set of measurement electronics. The process includes positioning the apparatus in a wire section of at least one of a paper, a cardboard, and a coater machine, irradiating at least one of the material web and the coating on the material web in the wire section with the at least one radiation source in the plurality of defined and different wavelength ranges, and measuring the intensity of the radiation that has been affected by the at least one of the material web and the coating on the material web with the at least one sensor. The at least one sensor detects only one of the defined and different wavelength ranges of the radiation at a time.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
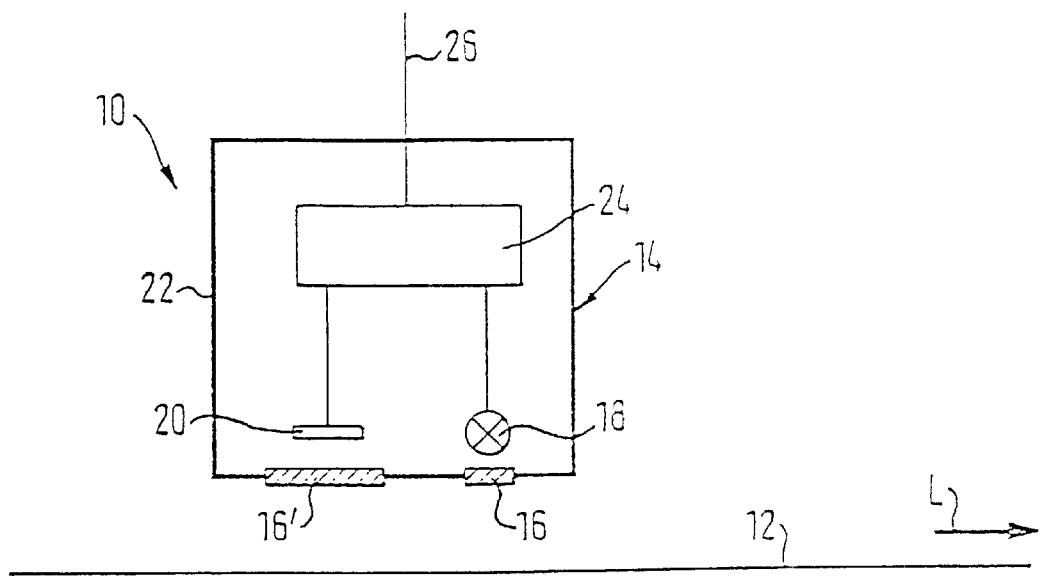
FIG. 1 schematically illustrates a first embodiment of a measurement system for the measurement of the cross-direction profile of specific properties of a web of material.

FIG. 1 schematically illustrates a measurement system 10 for measurement of the cross-direction profile of specific properties of a material web 12, e.g., a fibrous material web, in a paper and/or cardboard machine or a coating machine.

Measurement system 10 can include at least one stationary cross-direction profile measurement device 14 which can include a plurality of radiation (illumination) sources 18 distributed over a working width, i.e., perpendicular to the plane of FIG. 1, and at least one sensor 20 for measuring an intensity of the radiation (illumination) which has been affected by material web 12. Further, for a respective measurement point, a plurality of radiation sources 18 and/or a plurality of sensors 20 can be provided. It is also possible to provide, e.g., approximately 50 measurement points per meter. Of course, in practice, different measurement point densities can be utilized in accordance with the requirements of the user.

Material web 12 can be passed in the direction of arrow L under stationary cross-direction profile measurement device 14. Windows 16 and 16' are provided in housing 22 of stationary cross-direction profile measurement device 14 to be positioned adjacent to material web 12. Also adjacent windows 16 and 16', albeit on the side opposite material web 12, at least one optical radiation source 18 and at least one light-emitting diode or at least one sensor 20, e.g., a photodetector, are located within housing 22 of stationary cross-direction profile measurement device 14. Windows 16 and 16' are positioned at a distance from material web 12, and it can be expedient if the distance between the sensor(s) 20 and material web 12 or its coating lies in a range, e.g., between approximately 5 and approximately 20 mm.

Measurement and/or evaluation electronics 24 can be arranged within housing 22 and can be associated with stationary cross-direction profile measurement arrangement 14. Measurement and/or evaluation electronics 24 may be also be connected by at least one line 26 to a higher-order system, e.g., a process control system and/or a power supply.

The optical irradiation of material web 12 or its coating can occur, e.g., in a plurality of defined different wavelength ranges. Through the at least one radiation source 18, which is associated with a respective measurement point, the intensity of the radiation affected by material web 12 or its coating can be measured. Each sensor 20, which can likewise be associated with the measurement point in question, is arranged to detect only one of the defined different wavelength ranges of the radiation at a specific point in time.

In the exemplary embodiment, only the radiation reflected from material web 12 or its coating is detected by the sensor(s). In this manner, the space requirement necessary for operation can be reduced to a minimum.

Expediently, at least two stationary cross-direction profile measurement devices 14 can be positioned adjacent web 12 with a distance between them in direction of travel L. Thus, these stationary cross-direction profile measurement devices 14 can be provided in, e.g., the press section and/or dry section of the paper and/or cardboard machine. Such a stationary cross-direction profile measurement device 14 can also be used in a region of closed web travel. Moreover, it is also possible to provide stationary cross-direction profile measurement device 14 in the wire section and/or at the end of a paper and/or cardboard machine. To obtain the shortest possible control times, a respective stationary cross-direction profile measurement device 14 can be located, e.g., immediately before and/or immediately after at least one actuator or control element that is utilized to control the respective cross-direction profile being measured. For example, a "first" measurement device can be positioned close to the reel at the end of the machine, and a "second" measurement device can be positioned either in or closely before the headbox. Other advantageous locations for measurement devices can be between the position close to the reel and the headbox (or closely before the headbox). By way of example, it has been found that for determinations of basis weight and moisture profiles, it can be advantageous to locate the measurement device in or near the headbox, in the wet section, and in or shortly after the press section. This is because the basis weight and moisture profiles are generally controlled in these particular areas of the machine, e.g., basis weight in the headbox, moisture content in the press section.

Figure 2:
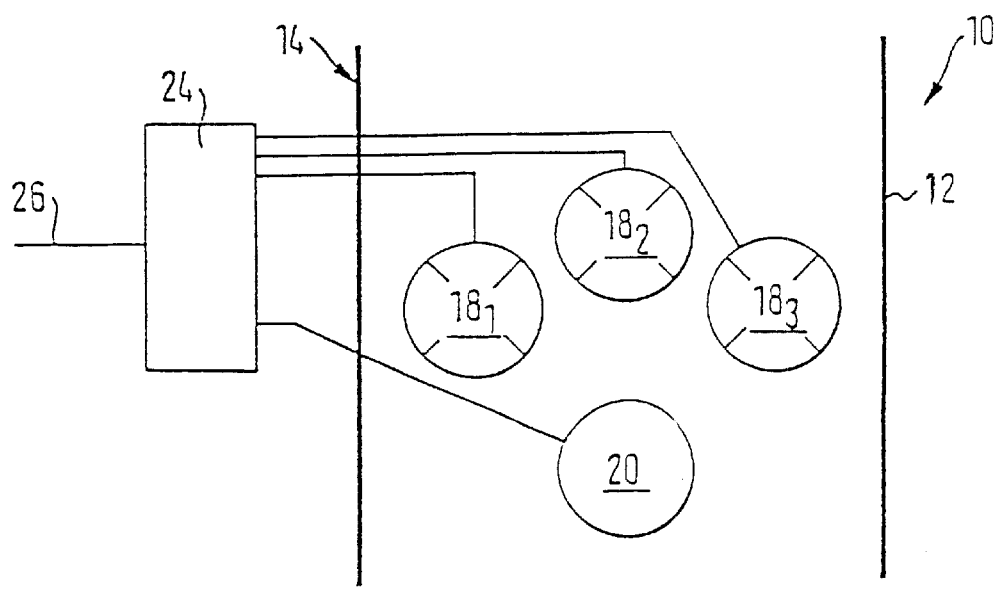
FIG. 2 schematically illustrates a further embodiment of the measurement system.

FIG. 2 schematically illustrates another further embodiment of stationary cross-direction profile measurement device 14 of measurement system 10. In this exemplary illustration, only a specific group of radiation sources $18_1$, $18_2$, and $18_3$ and a sensor 20 for one measurement point are depicted.

As is understood in FIG. 2, stationary cross-direction profile measurement device 14 include a housing 22 (not shown), which contains, for one measurement point, three optical radiation sources $18_1$, $18_2$, and $18_3$ and at least one sensor or photodetector 20. Both the radiation sources 18 and sensor(s) 20 are coupled to the measurement and/or evaluation electronics 24, which can be connected to a higher-order system, e.g., a process control system and/or a power supply, via line 26. In the exemplary embodiment, the measurement and/or evaluation electronics 24 can be located disposed outside of housing 22.

The three optical radiation sources $18_1$, $18_2$, and $18_3$ can be formed in the exemplary embodiment by an infrared light-emitting diode $18_1$, a red light-emitting diode $18_2$, and a blue light-emitting diode $18_3$. Consequently, material web 12 is irradiated by three radiation sources of different wavelength ranges.

It is further noted that the instant invention can utilize two sensors or photodetectors 20 per measurement point. In this case, the two sensors 20 should be located at different distances from radiation sources $18_1$, $18_2$, and $18_3$.

Measurement and/or evaluation electronics 24 control the time cycle of the irradiation and measurement, and can be located, e.g., in or on housing 22 (see FIG. 1) or remote from housing 22 (see FIG. 2).

Measurement and/or evaluation electronics 24 or a relevant higher-order system can deliver or forward at least one signal, which is representative of, e.g., surface weight, moisture, thickness, specific ingredients, and/or other properties of material web 12 or of the coating of material web 12.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

| List of Reference Characters | |
|---|---|
| 10 | measurement system |
| 12 | material web |
| 14 | stationary cross-direction profile measurement device |
| 16 | window |
| 16' | window |
| 18 | optical radiation source/light-emitting diode |
| $18_1$ | infrared light-emitting diode |
| $18_2$ | red light-emitting diode |
| $18_3$ | blue light-emitting diode |
| 20 | sensor/photodetector |
| 22 | housing |
| 24 | measurement and/or evaluation electronics |
| 26 | line |
| L | direction of travel of the web |

What is claimed:

1. A measurement system for measuring a cross-direction profile of specific properties of at least one of a material web and a coating on the material web, comprising:

at least one stationary cross-direction profile measurement device having a plurality of radiation sources, wherein each radiation source is adapted to irradiate the at least one of the material web and the coating on the material web in a plurality of defined and different wavelength ranges, and at least one sensor adapted to measure the intensity of radiation reflected by the at least one of the material web and the coating on the material web; and at least one measurement and/or evaluation electronics system, wherein each sensor detects only one of the defined different wavelength ranges of the radiation at a specific point in time.

2. The measurement system according to claim 1, the at least one stationary cross-direction profile measuring device comprising at least two stationary cross-direction profile measurement devices spaced in the direction of travel of the web.

3. The measurement system according to claim 2, wherein the at least one of the material web and the coating on the material web is located within at least one of a paper, a cardboard, and a coating machine, and wherein the at least two stationary cross-direction profile measurement devices are positioned such that one of the at least two stationary cross-directional profile measurement devices is positioned near an end of the at least one paper, cardboard, and coating machine, and another of the at least two stationary cross-directional profile measurement devices is positioned one of in and before a headbox of the at least one paper, cardboard, and coating machine.

4. The measurement system according to claim 1, further comprising at least one actuator and control element to adjust the cross-direction profile; and the at least one stationary cross-direction profile measurement device is arranged at least one of immediately before and immediately after at least one actuator and control element.

5. The measurement system according to claim 1, wherein the at least one stationary cross-direction profile measurement device is located in at least one of a press section and a dry section of one of a paper and cardboard machine.

6. The measurement system according to claim 1, the at least one stationary cross-direction profile measurement device is located in a region of closed web travel.

7. The measurement system according to claim 1, the at least one stationary cross-direction profile measurement device is located in at least one of a wire section and at an end of one of a paper and cardboard machine.

8. The measurement system according to claim 1, further comprising a filter device to filter out at least one of specific disturbance variables and the influence of at least one of an actuator and control element on a respective cross-direction profile.

9. The measurement system according to claim 1, at least one of the plurality of radiation sources and the at least one sensor being connected to at least one light guide.

10. The measurement system according to claim 1, the at least one stationary cross-direction profile measurement device is adapted to operate in the near infrared range (NIR).

11. The measurement system according to claim 1, the at least one stationary cross-direction profile measurement device is adapted to quantitatively detect at least one of surface weight, moisture, thickness, and specific ingredients of the at least one of the material web and the coating on the material web.

12. The measurement system according to claim 1, the at least one sensor is adapted to detect radiation passing through at least one of the at least one of the material web and the coating on the material web and a coating of the at least one of the material web and the coating on the material web.

13. The measurement system according to claim 1, the at least one stationary cross-direction profile measurement device comprising at least one optical radiation source adapted to irradiate the at least one of the material web and the coating on the material web, the at least one optical radiation source including at least one photodetector adapted to measure the intensity of the optical radiation affected by the at least one of the material web and the coating on the material web.

14. The measurement system according to claim 1, at least one of the at least one sensor and a filter unit has one of an adjustable spectral sensitivity and adjustable permeability.

15. The measurement system according to claim 1, the plurality of radiation sources comprising at least one light-emitting diode.

16. The measurement system according to claim 1, the plurality of radiation sources having different wavelength ranges, the plurality of radiation sources being adapted to irradiate the at least one of the material web and the coating on the material web.

17. The measurement system according to claim 16, the plurality of radiation sources,
wherein the at least one measurement and/or evaluation electronics is adapted to irradiate the at least one of the material web and the coating on the material web with at least one of a plurality of different wavelength ranges and chronologically consecutive combinations of the plurality of radiation sources.

18. The measurement system according to claim 1, the at least one stationary cross-direction profile measurement device comprising at least two sensors arranged at different distances relative to the plurality of radiation sources.

19. The measurement system according to claim 1, further comprising one of an additional sensor and an additional sensor pair adapted for use with the at least one radiation source.

20. The measurement system according to claim 1, the at least one radiation source comprising at least one of an infrared, a red, and a blue light-emitting diode.

21. The measurement system according to claim 1, the at least one stationary cross-direction profile measurement device comprising a plurality of stationary cross-direction profile measurement devices,
wherein the at least one measurement and/or evaluation electronics system is simultaneously associated with more than one stationary cross-direction profile measurement device of the plurality of stationary cross-direction profile measurement devices.

22. The measurement system according to claim 1, the at least one sensor comprising a digital camera.

23. A measurement system for measuring a cross-direction profile of specific properties of at least one of a material web and a coating on the material web, comprising:
at least one stationary cross-direction profile measurement device having at least one radiation source adapted to irradiate the at least one of the material web and the coating on the material web in a plurality of defined and different wavelength ranges, and at least one sensor adapted to measure the intensity of radiation affected by the at least one of the material web and the coating on the material web;
at least one measurement and/or evaluation electronics system, wherein each sensor detects only one of the defined different wavelength ranges of the radiation at a specific point in time;
the at least one stationary cross-direction profile measurement device comprising a device to spectrally divide optical radiation affected by the at least one of the material web and the coating on the material web on a sensor side; and
the device to spectrally divide optical radiation including a photodiode array with at least 16 sensors adapted to be acted upon by the divided radiation.

24. A measurement system for measuring a cross-direction profile of specific properties of at least one of a material web and a coating on the material web, comprising:
at least one stationary cross-direction profile measurement device having at least one radiation source adapted to irradiate the at least one of the material web and the coating on the material web in a plurality of defined and different wavelength ranges, and at least one sensor adapted to measure the intensity of radiation affected by the at least one of the material web and the coating on the material web;
at least one measurement and/or evaluation electronics system, wherein each sensor detects only one of the defined different wavelength ranges of the radiation at a specific point in time;
the at least one stationary cross-direction profile measurement device comprising a device to spectrally divide optical radiation affected by the at least one of the material web and the coating on the material web on a sensor side; and
the device to spectrally divide optical radiation including a photodiode array with at least 256 sensors adapted to be acted upon by the divided radiation.

25. A measurement system for measuring a cross-direction profile of specific properties of at least one of a material web and a coating on the material web, comprising:

at least one stationary cross-direction profile measurement device having at least one radiation source adapted to irradiate the at least one of the material web and the coating on the material web in a plurality of defined and different wavelength ranges, and at least one sensor adapted to measure the intensity of radiation affected by the at least one of the material web and the coating on the material web;

at least one measurement and/or evaluation electronics system, wherein each sensor detects only one of the defined different wavelength ranges of the radiation at a specific point in time; and the at least one radiation source comprising three optical radiation sources and the at least one sensor comprising at least one sensor adapted for use at each measurement point.

26. A measurement system for measuring a cross-direction profile of specific properties of at least one of a material web and a coating on the material web, comprising:

at least one stationary cross-direction profile measurement device having at least one radiation source adapted to irradiate the at least one of the material web and the coating on the material web in a plurality of defined and different wavelength ranges, and at least one sensor adapted to measure the intensity of radiation affected by the at least one of the material web and the coating on the material web;

at least one measurement and/or evaluation electronics system, wherein each sensor detects only one of the defined different wavelength ranges of the radiation at a specific point in time; and the at least one radiation source comprising at least one infrared, at least one red, and at least one blue light-emitting diode.

27. The measurement system according to claim 26, the at least one sensor comprising a plurality of sensors having different spectral sensitivities; and said at least one radiation source comprising only one radiation source.

28. A measurement system for measuring a cross-direction profile of specific properties of at least one of a material web and a coating on the material web, comprising:

at least one stationary cross-direction profile measurement device having at least one radiation source adapted to irradiate the at least one of the material web and the coating on the material web in a plurality of defined and different wavelength ranges, and at least one sensor adapted to measure the intensity of radiation affected by the at least one of the material web and the coating on the material web;

at least one measurement and/or evaluation electronics system, wherein each sensor detects only one of the defined different wavelength ranges of the radiation at a specific point in time; and the at least one radiation source comprising at least one light-emitting diode having a radiation angle within a range between approximately 12° and approximately 30°.

29. A process for measuring a cross-direction profile of specific properties of at least one of a material web and a coating on the material web, comprising:

irradiating the at least one of the material web and the coating on the material web with a plurality of defined and different wavelength ranges via a plurality of radiation sources; and measuring an intensity of radiation reflected by the at least one of the material web and the coating on the material web with at least one sensor;

wherein only one of the defined different wavelength ranges of the radiation is measured by each sensor at a specific point in time.

30. The process according to claim 29, further comprising adjusting the cross-direction profile with at least one of an actuator and a control element.

31. The process according to claim 29, wherein the irradiating and measuring are performed in a region of closed web travel.

32. The process according to claim 29, further comprising filtering out at least one of specific disturbance variables and the influence of at least one of an actuator and a control element on a respective cross-direction profile.

33. The process according to claim 29, further comprising operating the at least one radiation source in the near infrared range (NIR).

34. The process according to claim 29, further comprising quantitatively detecting at least one of surface weight, moisture, thickness, and specific ingredients of the at least one of the material web and the coating on the material web.

35. The process according to claim 29, further comprising detecting radiation passing through at least one of the at least one of the material web and the coating on the material web and a coating of the material web.

36. A process for determining a cross-direction profile of specific properties of at least one of a material web and a coating on the material web with an apparatus that includes a plurality of radiation sources, at least one sensor, and at least one set of measurement electronics, the process comprising:

positioning the apparatus in a press section of at least one of a paper, a cardboard, and a coater machine;

irradiating at least one of the material web and the coating on the material web in the press section in a plurality of defined and different wavelength ranges via each of the plurality of radiation sources; and measuring the intensity of the radiation reflected by the at least one of the material web and the coating on the material web with the at least one sensor, wherein the at least one sensor detects only one of the defined and different wavelength ranges of the radiation at a time.

37. A process for determining a cross-direction profile of specific properties of at least one of a material web and a coating on the material web with an apparatus that includes a plurality of radiation sources, at least one sensor, and at least one set of measurement electronics, the process comprising:

positioning the apparatus in a dryer section of at least one of a paper, a cardboard, and a coater machine;

irradiating at least one of the material web and the coating on the material web in the dryer section in a plurality of defined and different wavelength ranges from each of the plurality of radiation sources; and measuring the intensity of the radiation reflected by the at least one of the material web and the coating on the material web with the at least one sensor, wherein the at least one sensor detects only one of the defined and different wavelength ranges of the radiation at a time.

38. A process for determining a cross-direction profile of specific properties of at least one of a material web and a coating on the material web with an apparatus that includes a plurality of radiation sources, at least one sensor, and at least one set of measurement electronics, the process comprising:

positioning the apparatus in a wire section of at least one of a paper, a cardboard, and a coater machine;

irradiating at least one of the material web and the coating on the material web in the wire section in a plurality of defined and different wavelength ranges from the plurality of radiation sources; and measuring the intensity of the radiation reflected by the at least one of the material web and the coating on the material web with the at least one sensor, wherein the at least one sensor detects only one of the defined and different wavelength ranges of the radiation at a time.

* * * * *